(12) United States Patent
Yang

(10) Patent No.: US 9,139,818 B2
(45) Date of Patent: Sep. 22, 2015

(54) **HIGH EXPRESSION *ZYMOMONAS* PROMOTERS**

(71) Applicant: E I Du Pont De Nemours and Company, Wilmington, DE (US)

(72) Inventor: Jianjun Yang, Hockessin, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/037,666

(22) Filed: Sep. 26, 2013

(65) Prior Publication Data

US 2015/0087070 A1  Mar. 26, 2015

(51) Int. Cl.

| | |
|---|---|
| *C12P 21/06* | (2006.01) |
| *C12N 9/00* | (2006.01) |
| *C12N 1/20* | (2006.01) |
| *C12N 15/00* | (2006.01) |
| *C07H 21/04* | (2006.01) |
| *C12N 15/74* | (2006.01) |
| *C12N 9/04* | (2006.01) |
| *C12N 15/52* | (2006.01) |
| *C12N 1/22* | (2006.01) |
| *C12P 7/10* | (2006.01) |

(52) U.S. Cl.
CPC ............... *C12N 9/0006* (2013.01); *C12N 1/22* (2013.01); *C12N 15/52* (2013.01); *C12P 7/10* (2013.01); *C12N 15/00* (2013.01); *C12N 15/74* (2013.01)

(58) Field of Classification Search
None
See application file for complete search history.

(56) References Cited

U.S. PATENT DOCUMENTS

| | | |
|---|---|---|
| 5,514,583 A | 5/1996 | Picataggio et al. |
| 5,712,133 A | 1/1998 | Picataggio et al. |
| 5,726,053 A | 3/1998 | Picataggio et al. |
| 6,566,107 B1 | 5/2003 | Zhang |
| 7,223,575 B2 | 5/2007 | Zhang et al. |
| 7,741,119 B2 | 6/2010 | Viitanen et al. |
| 7,989,206 B2 | 8/2011 | Vitanen et al. |
| 7,998,722 B2 | 8/2011 | Viitanen et al. |
| 2011/0318801 A1 | 12/2011 | Kahsay et al. |

FOREIGN PATENT DOCUMENTS

| | | |
|---|---|---|
| WO | 2012006061 A1 | 1/2012 |

OTHER PUBLICATIONS

Yanase, Hideshi et al., Genetic Engineering of Zymobacter palmae for Production of Ethanol from Xylose, Applied and Environmental Microbiology, Apr. 2007, pp. 2592-2599, vol. 73, No. 8.
Feldmann, Sigrun D. et al., Pentose metabolism in *Zymomonas mobilis* wild-type and recombinant strains, Applied Microbiology and Biotechnology, 1992, pp. 354-361, vol. 38.
Zhang, Min et al., Metabolic Engineering of a Pentose Metabolism Pathway in Ethanologenic *Zymomonas mobilis*, Science, Jan. 13, 1995, pp. 240-243, vol. 267.
International Search Report, PCT International Application No. PCT/US2014/057386, Mailed Jan. 26, 2015.
Punt et al., Functional Elements in the Promoter Region of the Aspergillus Nidulans GPDA Gene Encoding Glyceraldehyde-3-Phosphate Dehydrogenase, Gene, vol. 93 (1990), pp. 101-109.
Liao et al., Characterization of a Highly Active Promoter, PBBGPD, in Beauveria Bassiana, Curr Microbiol, vol. 57(2008), pp. 121-126.

*Primary Examiner* — Christian Fronda

(57) ABSTRACT

Synthetic, derivative promoters for expression of chimeric genes in *Zymomonas, Zymobacter*, and related bacteria were created. The promoters have a C to T change in the nucleotide at position 90 of the *Z. mobilis* glyceraldehyde-3-phosphate dehydrogenase gene promoter. Promoters with this change have higher expression as compared to the native promoter from which they are derived and are useful for genetic engineering for expressing coding regions or regulatory RNA to obtain high levels of expressed proteins or regulatory RNAs.

13 Claims, 1 Drawing Sheet

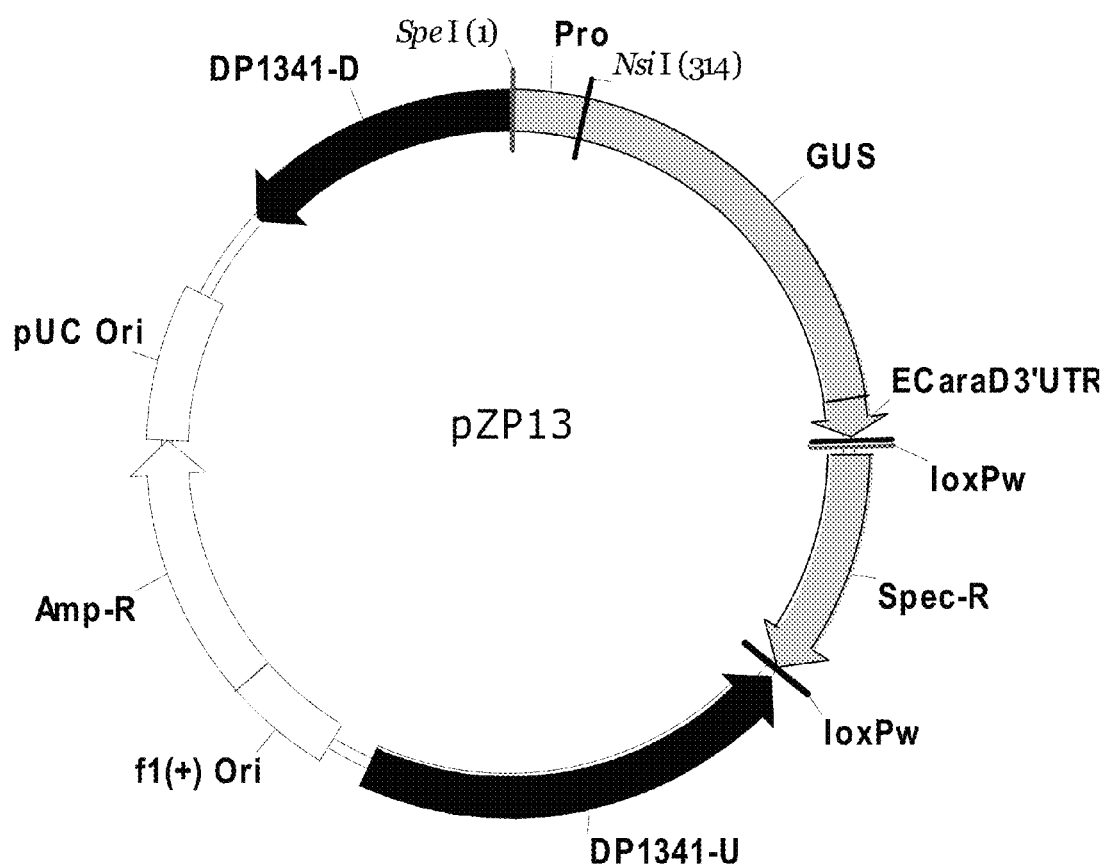

SEQUENCE LISTING

<160> NUMBER OF SEQ ID NOS: 16

<210> SEQ ID NO 1
<211> LENGTH: 305
<212> TYPE: DNA
<213> ORGANISM: Zymomonas mobilis

<400> SEQUENCE: 1
gttcgatcaa caacccgaat cctatcgtaa tgatgttttg cccgatcagc ctcaatcgac      60
aattttacgc gtttcgatcg aagcagggac gacaattggc tgggaacggt atactggaat     120
aaatggtctt cgttatggta ttgatgtttt tggtgcatcg gccccggcga atgatctata     180
tgctcatttc ggcttgaccg cagtcggcat cacgaacaag gtgttggccg cgatcgccgg     240
taagtcggca cgttaaaaaa tagctatgga atataatagc tacttaataa gttaggagaa     300
taaac                                                                 305

<210> SEQ ID NO 2
<211> LENGTH: 305
<212> TYPE: DNA
<213> ORGANISM: artificial sequence
<220> FEATURE:
<223> OTHER INFORMATION: Pgap with base change at position 90 nof C to T

<400> SEQUENCE: 2
gttcgatcaa caacccgaat cctatcgtaa tgatgttttg cccgatcagc ctcaatcgac      60
aattttacgc gtttcgatcg aagcagggat gacaattggc tgggaacggt atactggaat     120
aaatggtctt cgttatggta ttgatgtttt tggtgcatcg gccccggcga atgatctata     180
tgctcatttc ggcttgaccg cagtcggcat cacgaacaag gtgttggccg cgatcgccgg     240
taagtcggca cgttaaaaaa tagctatgga atataatagc tacttaataa gttaggagaa     300
taaac                                                                 305

<210> SEQ ID NO 3
<211> LENGTH: 305
<212> TYPE: DNA
<213> ORGANISM: Zymomonas mobilis

<400> SEQUENCE: 3
gttcgatcaa caacccgaat cctatcgtaa tgatgttttg cccgatcagc ctcaatcgac      60
aattttacgc gtttcgatcg aagcagggac gacaattggc tgggaacggt atactggaat     120
aaatggtctt cgttatggta ttgatgtttt tggtgcatcg gccccggcga atgatctata     180
tgctcatttc ggcttgaccg cagtcggcat cacgaacaag gtgttggccg cgatcgccgg     240
taagtcggca cgttaaaaaa tagctatgga atatagtagc tacttaataa gttaggagaa     300
taaac                                                                 305

<210> SEQ ID NO 4
<211> LENGTH: 305
<212> TYPE: DNA
<213> ORGANISM: artificial sequence
<220> FEATURE:
<223> OTHER INFORMATION: Pgap with change of C to T at position 90 in
      ZM4 sequence

<400> SEQUENCE: 4
gttcgatcaa caacccgaat cctatcgtaa tgatgttttg cccgatcagc ctcaatcgac      60
aattttacgc gtttcgatcg aagcagggat gacaattggc tgggaacggt atactggaat     120

```
aaatggtctt cgttatggta ttgatgttttt tggtgcatcg gccccggcga atgatctata    180
tgctcatttc ggcttgaccg cagtcggcat cacgaacaag gtgttggccg cgatcgccgg    240
taagtcggca cgttaaaaaa tagctatgga atatagtagc tacttaataa gttaggagaa    300
taaac                                                                 305

<210> SEQ ID NO 5
<211> LENGTH: 304
<212> TYPE: DNA
<213> ORGANISM: artificial sequence
<220> FEATURE:
<223> OTHER INFORMATION: Pgap in pZB4 - has deletion of T at position
      285

<400> SEQUENCE: 5
gttcgatcaa caacccgaat cctatcgtaa tgatgttttg cccgatcagc ctcaatcgac     60
aattttacgc gtttcgatcg aagcagggac gacaattggc tgggaacggt atactggaat   120
aaatggtctt cgttatggta ttgatgttttt tggtgcatcg gccccggcga atgatctata   180
tgctcatttc ggcttgaccg cagtcggcat cacgaacaag gtgttggccg cgatcgccgg   240
taagtcggca cgttaaaaaa tagctatgga atataatagc tactaataag ttaggagaat   300
aaac                                                                 304

<210> SEQ ID NO 6
<211> LENGTH: 304
<212> TYPE: DNA
<213> ORGANISM: artificial sequence
<220> FEATURE:
<223> OTHER INFORMATION: pZB4 Pgap with C to T change at position 90

<400> SEQUENCE: 6
gttcgatcaa caacccgaat cctatcgtaa tgatgttttg cccgatcagc ctcaatcgac     60
aattttacgc gtttcgatcg aagcagggat gacaattggc tgggaacggt atactggaat   120
aaatggtctt cgttatggta ttgatgttttt tggtgcatcg gccccggcga atgatctata   180
tgctcatttc ggcttgaccg cagtcggcat cacgaacaag gtgttggccg cgatcgccgg   240
taagtcggca cgttaaaaaa tagctatgga atataatagc tactaataag ttaggagaat   300
aaac                                                                 304

<210> SEQ ID NO 7
<211> LENGTH: 304
<212> TYPE: DNA
<213> ORGANISM: artificial sequence
<220> FEATURE:
<223> OTHER INFORMATION: Pgap of ZM4 with T deletion at position 285
      and C to T change at position 90

<400> SEQUENCE: 7
gttcgatcaa caacccgaat cctatcgtaa tgatgttttg cccgatcagc ctcaatcgac     60
aattttacgc gtttcgatcg aagcagggat gacaattggc tgggaacggt atactggaat   120
aaatggtctt cgttatggta ttgatgttttt tggtgcatcg gccccggcga atgatctata   180
tgctcatttc ggcttgaccg cagtcggcat cacgaacaag gtgttggccg cgatcgccgg   240
taagtcggca cgttaaaaaa tagctatgga atatagtagc tactaataag ttaggagaat   300
aaac                                                                 304

<210> SEQ ID NO 8
<211> LENGTH: 1951
```

<212> TYPE: DNA
<213> ORGANISM: Zymomonas mobilis

<400> SEQUENCE: 8

```
aactgccacc acccataaat cccagcgggt ttattttaaa aataaaacaa atgataacca      60
aaacgatcac gccgccgata ccgaaacggc aacgacaaa gccgagtaag ccgctaatca     120
ggttaaaccc gccgccaccg ccgttattac caccgctaaa gtcttcacca cgttcgtctt     180
cgacgttatc gctgcttcgg tagtcatcaa gccgcattat gccttccc aattttaccc      240
gcaggcctat ttataggccg acagcgggtt ttatctatag ctttcatttt tttgtgtttt     300
tttgaaaaaa aacgcttgca gaacacatag ctgattgtta tacgcgcttc acacccaacg     360
cggtgattga catagtgttc cctgatagct cagcggtaga gcgtccgact gttaatcggc     420
aggtcgtagg ttcgaatcct actcggggag ccatttcaac gatagtcctt atagttttat     480
tttctcttta aaaatttatc ttatttccga tcaatcggtt atatttcgcc tgatagattc     540
aagacattct gtattgggat tgtctgaata tatttcgggt agatctgttt aaagtggttt     600
ttttgtccac tttcctaatt aggttatttc cataacgtga cccaatagcg tggccgtgag     660
cgcttggctg ccgcggaata gggatatttt cttttttcga gataccgcca gccattaagc     720
cattaagcca ttaagccatt aagccattaa gccattaagc cattaagcca ttaagatatc     780
gctactcatt ctttcggcaa ggaaaaaggt gattagtcgt tatttggggt aataaatgtt     840
tatcctcgga tcgagatttc ttgaataaag aaggacgagt ggttttcttc atttgagcct     900
ttttctttt ttgcttttc tatttcgctg gaaacacccc ttttcaccta ttccagatag      960
attgtcccct ttcgctttt taaagcattg atcgtagaaa tcactccgat ggtcgtatga    1020
cagcgtttc tttggaaagc ggggttttac agcctttatc aatagggtca ggatggggga    1080
atcatcctct atatggagaa gtatgatgtc ccctatttcg ataccctcta tccgtctgaa    1140
tgacggcaat gatttgcctg cggtaggctt tggcacctat aaactcaatg gttcggccgg    1200
tgtttccgat atcgttagcg cgattaaagt cggataccgc ttgctcgatt ctgcctttaa    1260
ttatgagaat gaaggtgctg taggcgaagc tgttcgcgag gccggtattg cccgtgataa    1320
attgcggatc gtgtccaaat taccggggcg acatcatcat tttgaagagg ccattgcaac    1380
ggtcgaggag tcactttatc gggcacagct tgattattat gatctctatc tgattcattg    1440
gcctaatccg agcaaagatc tctatgtcga ggcgtggcag gccttgattg aagcccgtaa    1500
aaaagggtta atccgttcga ttggtgtctg taacttttta ccagaacatc tggaaaggct    1560
gattaaagag acgggtgtaa cgccggttgt caatcaggtg gaattgcatc cctatttcc     1620
gcaggaagag cagcgggcat gggataaagc ccatggcatt gttaccgagt catggagtcc    1680
tttgggacgt gccagcaagt tgctacagga cgacacgatt aaaaaaattg cggatcgctt    1740
gggtaagtct atcccgcaag ttattttgcg ttggcatgtc cagcttggag cgataccgat    1800
tcctaaagct tctagcaaag agcgtcagat tgaaaatcta tccttgtttg atttcgagct    1860
gtcgccgcag gatgtagaaa taatcgcgac tttagcacgg cctgatggac gcttggctga    1920
ccaagaccct gcccgctatg aagaattta a                                    1951
```

<210> SEQ ID NO 9
<211> LENGTH: 1255
<212> TYPE: DNA
<213> ORGANISM: Zymomonas mobilis

<400> SEQUENCE: 9

-continued

| | |
|---|---|
| aataatcccg acagcagttg cattatgatg ggttaaatgc accagaacta gccagtcctg | 60 |
| tgcaatgcgt tgcatccatg tcccgatatt ggacacgaac attccactta tccaaaggcg | 120 |
| ataattgaag ctgttcagtg accggaaggt tccatggaaa agttttttca tcagaggctc | 180 |
| gctctatttt tacatgccga gcagaagcgc cttgatccgc tagcatccca tattgggagg | 240 |
| atgtttttgt gcgccagaaa agcggaaaaa atatctacga tcatagacgg tcgtcagatt | 300 |
| ttccggtgat tggcttgttc aagctatgcg tcaagagcgg gatatcaagc gtcatgataa | 360 |
| gaaaaaggat acaggataga cgcttttgaa aaaggccatc gctgtatcct aagagtattt | 420 |
| tagttgataa ttttttactaa ataaggcgta taaccttatg cttttacggt aaaatattta | 480 |
| ttattttta ttgaccgaat atgtgttttt cgctttcgca aagacatgaa taccatttca | 540 |
| tctcaacaga atttaactat caatatcatg atggaaggta tcgcaaacgg ctggatcgcc | 600 |
| gctatcaatc ccgcgtttga gccagcgcat tctttccgca gatgtgccat gagtgaaact | 660 |
| ttcaggaacg gggcgcatcc ctgcggcttt ctctaaggta tcgtcgccaa tagcctgcgc | 720 |
| tgcccgcata ccttcttcga catcgccctc ttctatccgg tcgcggttat gcgctgccca | 780 |
| gactccggca tagcaatcgg cctgtaattc cattctcacc tgtagggcat tagcggcagc | 840 |
| tttgccgaca ttagcttgtt gttcgcggat ttggtcggat aagcccatta aatcttgcac | 900 |
| atgatgcccg acttcatggg cgataacata ggcttgggca aaatcaccgc tggcaggaag | 960 |
| cggttgacca gttcattata gaaatctgta tcgagataaa cgcgctgatc tgctgggcag | 1020 |
| taaaaaggcc ccatcgccga ttctgctgca ccgcagcctg aacgacctct ttgactataa | 1080 |
| aagaccaatg ttgtcggttt atattttta ccagcatcag cgaaaatctt gccccatgtg | 1140 |
| tcttcggtac tagccaagac acggcaggag aaaaggcttg cggcgttaag ttggcaggcc | 1200 |
| tgttgtgccg aacgaacaga atgcacctga tgaggtgcca tcgcgggttg tgtcg | 1255 |

<210> SEQ ID NO 10
<211> LENGTH: 1815
<212> TYPE: DNA
<213> ORGANISM: Escherichia coli

<400> SEQUENCE: 10

| | |
|---|---|
| atgcatgtac gtcctgtaga aaccccaacc cgtgaaatca aaaaactcga cggcctgtgg | 60 |
| gcattcagtc tggatcgcga aaactgtgga attgatcagc gttggtggga aagcgcgtta | 120 |
| caagaaagcc gggcaattgc tgtgccaggc agttttaacg atcagttcgc cgatgcagat | 180 |
| attcgtaatt atgcgggcaa cgtctggtat cagcgcgaag tctttatacc gaaaggttgg | 240 |
| gcaggccagc gtatcgtgct gcgtttcgat gcggtcactc attacggcaa agtgtgggtc | 300 |
| aataatcagg aagtgatgga gcatcagggc ggctatacgc catttgaagc cgatgtcacg | 360 |
| ccgtatgtta ttgccgggaa aagtgtacgt atcaccgttt gtgtgaacaa cgaactgaac | 420 |
| tggcagacta tcccgccggg aatggtgatt accgacgaaa acggcaagaa aaagcagtct | 480 |
| tacttccatg atttctttaa ctatgccgga atccatcgca gcgtaatgct ctacaccacg | 540 |
| ccgaacacct gggtggacga tatcaccgtg gtgacgcatg tcgcgcaaga ctgtaaccac | 600 |
| gcgtctgttg actggcaggt ggtggccaat ggtgatgtca gcgttgaact gcgtgatgcg | 660 |
| gatcaacagg tggttgcaac tggacaaggc actagcggga ctttgcaagt ggtgaatccg | 720 |
| cacctctggc aaccgggtga aggttatctc tatgaactgt gcgtcacagc caaaagccag | 780 |
| acagagtgtg atatctaccc gcttcgcgtc ggcatccggt cagtggcagt gaagggcgaa | 840 |
| cagttcctga ttaaccacaa accgttctac tttactggct ttggtcgtca tgaagatgcg | 900 |

```
gacttgcgtg gcaaaggatt cgataacgtg ctgatggtgc acgaccacgc attaatggac      960
tggattgggg ccaactccta ccgtacctcg cattacccct acgctgaaga gatgctcgac     1020
tgggcagatg aacatggcat cgtggtgatt gatgaaactg ctgctgtcgg ctttaacctc     1080
tctttaggca ttggtttcga agcgggcaac aagccgaaag aactgtacag cgaagaggca     1140
gtcaacgggg aaactcagca agcgcactta caggcgatta agagctgat agcgcgtgac      1200 aaaaaccacc caagcgtggt gatgtggagt attgccaacg aaccggatac ccgtccgcaa     1260
ggtgcacggg aatatttcgc gccactggcg gaagcaacgc gtaaactcga cccgacgcgt     1320
ccgatcacct gcgtcaatgt aatgttctgc gacgctcaca ccgataccat cagcgatctc     1380
tttgatgtgc tgtgcctgaa ccgttattac ggatggtatg tccaaagcgg cgatttggaa     1440
acggcagaga aggtactgga aaagaactt ctggcctggc aggagaaact gcatcagccg      1500
attatcatca ccgaatacgg cgtggatacg ttagccgggc tgcactcaat gtacaccgac     1560
atgtggagtg aagagtatca gtgtgcatgg ctggatatgt atcaccgcgt ctttgatcgc     1620
gtcagcgccg tcgtcggtga acaggtatgg aatttcgccg atttttgcga ctcgcaaggc     1680
atattgcgcg ttggcggtaa caagaaaggg atcttcactc gcgaccgcaa accgaagtcg     1740
gcggcttttc tgctgcaaaa acgctggact ggcatgaact tcggtgaaaa accgcagcag     1800
ggaggcaaac aatga                                                     1815

<210> SEQ ID NO 11
<211> LENGTH: 166
<212> TYPE: DNA
<213> ORGANISM: Escherichia coli

<400> SEQUENCE: 11
tgactgtata aaaccacagc caatcaaacg aaaccaggct atactcaagc ctggtttttt      60
gatggatttt cagcgtggcg caggcaggtt ttatcttaac ccgacactgg cgggacaccc     120
cgcaagggac agaagtctcc ttctggctgg cgacggacaa cgggcc                   166

<210> SEQ ID NO 12
<211> LENGTH: 1014
<212> TYPE: DNA
<213> ORGANISM: artificial sequence
<220> FEATURE:
<223> OTHER INFORMATION: Spec-R expression cassette

<400> SEQUENCE: 12
agcacaggat gacgcctaac aattcattca agccgacacc gcttcgcggc gcggcttaat      60
tcaggagtta acatcatga gggaagcggt gatcgccgaa gtatcgactc aactatcaga     120
ggtagttggc gtcatcgagc gccatctcga accgacgttg ctggccgtac atttgtacgg     180
ctccgcagtg gatggcggcc tgaagccaca cagtgatatt gatttgctgg ttacggtgac     240
tgtaaggctt gatgaaacaa cgcggcgagc tttgatcaac gaccttttgg aaacttcggc     300
ttcccctgga gagagcgaga ttctccgcgc tgtagaagtc accattgttg tgcacgacga     360
catcattccg tggcgttatc cagctaagcg cgaactgcaa tttggagaat ggcagcgcaa     420
tgacattctt gcaggtatct tcgagccagc cacgatcgac attgatctgg ctatcttgct     480
gacaaaagca agagaacata gcgttgcctt ggtaggtcca gcggcggagg aactctttga     540
tccggttcct gaacaggatc tatttgaggc gctaaatgaa accttaacgc tatggaactc     600
gccgcccgac tgggctggcg atgagcgaaa tgtagtgctt acgttgtccc gcatttggta     660
```

```
cagcgcagta accggcaaaa tcgcgccgaa ggatgtcgct gccgactggg caatggagcg    720
cctgccggcc cagtatcagc ccgtcatact tgaagctagg caggcttatc ttggacaaga    780
agatcgcttg gcctcgcgcg cagatcagtt ggaagaattt gttcactacg tgaaaggcga    840
gatcaccaag gtagtcggca ataatgtct aacaattcgt tcaagccgac gccgcttcgc    900
ggcgcggctt aactcaagcg ttagagagct ggggaagact atgcgcgatc tgttgaaggt    960
ggttctaagc ctcgtacttg cgatggcatc ggggcaggca cttgctgacc tgcc         1014
```

<210> SEQ ID NO 13
<211> LENGTH: 9512
<212> TYPE: DNA
<213> ORGANISM: artificial sequence
<220> FEATURE:
<223> OTHER INFORMATION: constructed plasmid

<400> SEQUENCE: 13

```
ctagttcgat caacaacccg aatcctatcg taatgatgtt ttgcccgatc agcctcaatc      60
gacaatttta cgcgtttcga tcgaagcagg gacgacaatt ggctgggaac ggtatactgg    120
aataaatggt cttcgttatg gtattgatgt ttttggtgca tcggccccgg cgaatgatct    180
atatgctcat ttcggcttga ccgcagtcgg catcacgaac aaggtgttgg ccgcgatcgc    240
cggtaagtcg gcacgttaaa aaatagctat ggaatataat agctacttaa taagttagga    300
gaataaacat gcatgtacgt cctgtagaaa ccccaacccg tgaaatcaaa aaactcgacg    360
gcctgtgggc attcagtctg gatcgcgaaa actgtggaat tgatcagcgt tggtgggaaa    420
gcgcgttaca agaaagccgg gcaattgctg tgccaggcag ttttaacgat cagttcgccg    480
atgcagatat tcgtaattat gcgggcaacg tctggtatca gcgcgaagtc tttataccga    540
aaggttgggc aggccagcgt atcgtgctgc gtttcgatgc ggtcactcat tacggcaaag    600
tgtgggtcaa taatcaggaa gtgatggagc atcagggcgg ctatacgcca tttgaagccg    660
atgtcacgcc gtatgttatt gccgggaaaa gtgtacgtat caccgtttgt gtgaacaacg    720
aactgaactg gcagactatc ccgccgggaa tggtgattac cgacgaaaac ggcaagaaaa    780
agcagtctta cttccatgat ttctttaact atgccggaat ccatcgcagc gtaatgctct    840
acaccacgcc gaacacctgg gtggacgata tcaccgtggt gacgcatgtc gcgcaagact    900
gtaaccacgc gtctgttgac tggcaggtgg tggccaatgg tgatgtcagc gttgaactgc    960
gtgatgcgga tcaacaggtg gttgcaactg gacaaggcac tagcgggact tgcaagtgg   1020 tgaatccgca cctctggcaa ccgggtgaag gttatctcta tgaactgtgc gtcacagcca   1080
aaagccagac agagtgtgat atctacccgc ttcgcgtcgg catccggtca gtggcagtga   1140
agggcgaaca gttcctgatt aaccacaaac cgttctactt tactggcttt ggtcgtcatg   1200
aagatgcgga cttgcgtggc aaaggattcg ataacgtgct gatggtgcac gaccacgcat   1260
taatggactg gattgggccc aactcctacc gtacctcgca ttacccttac gctgaagaga   1320
tgctcgactg ggcagatgaa catggcatcg tggtgattga tgaaactgct gctgtcggct   1380
ttaacctctc tttaggcatt ggtttcgaag cgggcaacaa gccgaaagaa ctgtacagcg   1440
aagaggcagt caacggggaa actcagcaag cgcacttaca ggcgattaaa gagctgatag   1500
cgcgtgacaa aaaccaccca agcgtggtga tgtggagtat tgccaacgaa ccggataccc   1560
gtccgcaagg tgcacgggaa tatttcgcgc cactggcgga agcaacgcgt aaactcgacc   1620
cgacgcgtcc gatcacctgc gtcaatgtaa tgttctgcga cgctcacacc gataccatca   1680
gcgatctctt tgatgtgctg tgcctgaacc gttattacgg atggtatgtc caaagcggcg   1740
```

```
atttggaaac ggcagagaag gtactggaaa aagaacttct ggcctggcag gagaaactgc    1800
atcagccgat tatcatcacc gaatacggcg tggatacgtt agccgggctg cactcaatgt    1860
acaccgacat gtggagtgaa gagtatcagt gtgcatggct ggatatgtat caccgcgtct    1920
ttgatcgcgt cagcgccgtc gtcggtgaac aggtatggaa tttcgccgat tttgcgacct    1980
cgcaaggcat attgcgcgtt ggcggtaaca agaaagggat cttcactcgc gaccgcaaac    2040
cgaagtcggc ggcttttctg ctgcaaaaac gctggactgg catgaacttc ggtgaaaaac    2100
cgcagcaggg aggcaaacaa tgatctagat gactgtataa aaccacagcc aatcaaacga    2160
aaccaggcta tactcaagcc tggttttttg atggattttc agcgtggcgc aggcaggttt    2220
tatcttaacc cgacactggc gggacacccc gcaagggaca aagtctcct tctggctggc    2280 gacggacaac gggccaagct tggaagggcc ggccaagctt gaattcgcga tcgcataact    2340
tcgtataatg tatgctatac gaagttatgc ggccgcagca caggatgacg cctaacaatt    2400
cattcaagcc gacaccgctt cgcggcgcgg cttaattcag gagttaaaca tcatgaggga    2460
agcggtgatc gccgaagtat cgactcaact atcagaggta gttggcgtca tcgagcgcca    2520
tctcgaaccg acgttgctgg ccgtacattt gtacggctcc gcagtggatg gcggcctgaa    2580
gccacacagt gatattgatt tgctggttac ggtgactgta aggcttgatg aaacaacgcg    2640
gcgagctttg atcaacgacc ttttggaaac ttcggcttcc cctggagaga gcgagattct    2700
ccgcgctgta gaagtcacca ttgttgtgca cgacgacatc attccgtggc gttatccagc    2760
taagcgcgaa ctgcaatttg gagaatggca gcgcaatgac attcttgcag gtatcttcga    2820
gccagccacg atcgacattg atctggctat cttgctgaca aaagcaagag aacatagcgt    2880
tgccttggta ggtccagcgg cggaggaact ctttgatccg gttcctgaac aggatctatt    2940
tgaggcgcta aatgaaacct taacgctatg gaactcgccg cccgactggg ctggcgatga    3000
gcgaaatgta gtgcttacgt tgtcccgcat ttggtacagc gcagtaaccg gcaaaatcgc    3060
gccgaaggat gtcgctgccg actgggcaat ggagcgcctg ccggcccagt atcagcccgt    3120
catacttgaa gctaggcagg cttatcttgg acaagaagat cgcttggcct cgcgcgcaga    3180
tcagttggaa gaatttgttc actacgtgaa aggcgagatc accaaggtag tcggcaaata    3240
atgtctaaca attcgttcaa gccgacgccg cttcgcggcg cggcttaact caagcgttag    3300
agagctgggg aagactatgc gcgatctgtt gaaggtggtt ctaagcctcg tacttgcgat    3360
ggcatcgggg caggcacttg ctgacctgcc ttaattaaat aacttcgtat aatgtatgct    3420
atacgaagtt atgccggcc aactgccacc acccataaat cccagcgggt ttatttaaa    3480 aataaaacaa atgataacca aaacgatcac gccgccgata ccgaaacggc caacgacaaa    3540
gccgagtaag ccgctaatca ggttaaaccc gccgccaccg ccgttattac caccgctaaa    3600
gtcttcacca cgttcgtctt cgacgttatc gctgcttcgg tagtcatcaa gccgcattat    3660
gcaccttccc aatttacccc gcaggcctat ttataggccg acagcgggtt ttatctatag    3720
ctttcatttt tttgtgtttt tttgaaaaaa aacgcttgca gaacacatag ctgattgtta    3780
tacgcgcttc acacccaacg cggtgattga catagtgttc cctgatagct cagcggtaga    3840
gcgtccgact gttaatcggc aggtcgtagg ttcgaatcct actcggggag ccatttcaac    3900
gatagtcctt atagttttat tttctcttta aaaatttatc ttatttccga tcaatcggtt    3960
atatttcgcc tgatagattc aagacattct gtattgggat tgtctgaata tatttcgggt    4020
agatctgttt aaagtggttt ttttgtccac tttcctaatt aggttatttc cataacgtga    4080
```

```
cccaatagcg tggccgtgag cgcttggctg ccgcggaata gggatatttt cttttttcga    4140
gataccgcca gccattaagc cattaagcca ttaagccatt aagccattaa gccattaagc    4200
cattaagcca ttaagatatc gctactcatt ctttcggcaa ggaaaaaggt gattagtcgt    4260
tatttggggt aataaatgtt tatcctcgga tcgagatttc ttgaataaag aaggacgagt    4320
ggttttcttc atttgagcct ttttctttt ttgcttttc tatttcgctg gaaacacccc     4380
ttttcaccta ttccagatag attgtcccct ttcgctttt taaagcattg atcgtagaaa    4440
tcactccgat ggtcgtatga cagcgttttc tttggaaagc ggggttttac agcctttatc    4500
aatagggtca ggatggggga atcatcctct atatggagaa gtatgatgtc cctatttcg    4560
ataccctcta tccgtctgaa tgacggcaat gatttgcctg cggtaggctt tggcacctat    4620
aaactcaatg gttcggccgg tgtttccgat atcgttagcg cgattaaagt cggataccgc    4680
ttgctcgatt ctgcctttaa ttatgagaat gaaggtgctg taggcgaagc tgttcgcgag    4740
gccggtattg cccgtgataa attgcggatc gtgtccaaat taccggggcg acatcatcat    4800
tttgaagagg ccattgcaac ggtcgaggag tcactttatc gggcacagct tgattattat    4860
gatctctatc tgattcattg gcctaatccg agcaaagatc tctatgtcga ggcgtggcag    4920
gccttgattg aagcccgtaa aaagggtta atccgttcga ttggtgtctg taactttta     4980
ccagaacatc tggaaaggct gattaaagag acgggtgtaa cgccggttgt caatcaggtg    5040
gaattgcatc cctattttcc gcaggaagag cagcgggcat gggataaagc ccatggcatt    5100
gttaccgagt catggagtcc tttgggacgt gccagcaagt tgctacagga cgacacgatt    5160
aaaaaaattg cggatcgctt gggtaagtct atcccgcaag ttattttgcg ttggcatgtc    5220
cagcttggag cgataccgat tcctaaagct tctagcaaag agcgtcagat tgaaaatcta    5280
tccttgtttg atttcgagct gtcgccgcag gatgtagaaa taatcgcgac tttagcacgg    5340
cctgatggac gcttggctga ccaagaccct gcccgctatg aagaatttta aggtacccaa    5400
ttcgccctat agtgagtcgt attacgcgcg ctcactggcc gtcgttttac aacgtcgtga    5460
ctgggaaaac cctggcgtta cccaacttaa tcgccttgca gcacatcccc ctttcgccag    5520
ctggcgtaat agcgaagagg cccgcaccga tcgcccttcc caacagttgc gcagcctgaa    5580
tggcgaatgg gacgcgccct gtagcggcgc attaagcgcg gcgggtgtgg tggttacgcg    5640
cagcgtgacc gctacacttg ccagcgccct agcgcccgct cctttcgctt tcttcccttc    5700
ctttctcgcc acgttcgccg gctttccccg tcaagctcta atcgggggc tccctttagg     5760
gttccgattt agtgctttac ggcacctcga ccccaaaaaa cttgattagg gtgatggttc    5820
acgtagtggg ccatcgccct gatagacggt ttttcgccct ttgacgttgg agtccacgtt    5880
ctttaatagt ggactcttgt tccaaactgg aacaacactc aaccctatct cggtctattc    5940
ttttgattta aagggattt tgccgatttc ggcctattgg ttaaaaatg agctgattta     6000
acaaaaattt aacgcgaatt ttaacaaaat attaacgctt acaatttagg tggcactttt    6060
cggggaaatg tgcgcggaac ccctatttgt ttatttttct aaatacattc aaatatgtat    6120
ccgctcatga caataaacc ctgataaatg cttcaataat attgaaaaag gaagagtatg     6180
agtattcaac atttccgtgt cgcccttatt ccctttttg cggcattttg ccttcctgtt     6240
tttgctcacc cagaaacgct ggtgaaagta aaagatgctg aagatcagtt gggtgcacga    6300
gtgggttaca tcgaactgga tctcaacagc ggtaagatcc ttgagagttt tcgccccgaa    6360
gaacgttttc caatgatgag cacttttaaa gttctgctat gtggcgcggt attatcccgt    6420
attgacgccg ggcaagagca actcggtcgc cgcatacact attctcagaa tgacttggtt    6480
```

```
gagtactcac cagtcacaga aaagcatctt acggatggca tgacagtaag agaattatgc    6540
agtgctgcca taaccatgag tgataacact gcggccaact tacttctgac aacgatcgga    6600
ggaccgaagg agctaaccgc ttttttgcac aacatggggg atcatgtaac tcgccttgat    6660
cgttgggaac cggagctgaa tgaagccata ccaaacgacg agcgtgacac cacgatgcct    6720
gtagcaatgg caacaacgtt gcgcaaacta ttaactggcg aactacttac tctagcttcc    6780
cggcaacaat taatagactg gatggaggcg ataaagttg caggaccact tctgcgctcg     6840
gcccttccgg ctggctggtt tattgctgat aaatctggag ccggtgagcg tgggtctcgc    6900
ggtatcattg cagcactggg gccagatggt aagccctccc gtatcgtagt tatctacacg    6960
acggggagtc aggcaactat ggatgaacga atagacaga tcgctgagat aggtgcctca     7020
ctgattaagc attggtaact gtcagaccaa gtttactcat atatacttta gattgattta    7080
aaacttcatt tttaatttaa aaggatctag gtgaagatcc ttttgataa tctcatgacc     7140 aaaatccctt aacgtgagtt ttcgttccac tgagcgtcag accccgtaga aaagatcaaa    7200
ggatcttctt gagatccttt ttttctgcgc gtaatctgct gcttgcaaac aaaaaaacca    7260
ccgctaccag cggtggtttg tttgccggat caagagctac caactctttt tccgaaggta    7320
actggcttca gcagagcgca gataccaaat actgtccttc tagtgtagcc gtagttaggc    7380
caccacttca agaactctgt agcaccgcct acatacctcg ctctgctaat cctgttacca    7440
gtggctgctg ccagtggcga taagtcgtgt cttaccgggt tggactcaag acgatagtta    7500
ccggataagg cgcagcggtc gggctgaacg gggggttcgt gcacacagcc cagcttggag    7560
cgaacgacct acaccgaact gagatacccta cagcgtgagc tatgagaaag cgccacgctt    7620
cccgaaggga gaaaggcgga caggtatccg gtaagcggca gggtcggaac aggagagcgc    7680
acgagggagc ttccaggggg aaacgcctgg tatctttata gtcctgtcgg gtttcgccac    7740
ctctgacttg agcgtcgatt tttgtgatgc tcgtcagggg ggcggagcct atggaaaaac    7800
gccagcaacg cggccttttt acggttcctg gccttttgct ggccttttgc tcacatgttc    7860
tttcctgcgt tatcccctga ttctgtggat aaccgtatta ccgcctttga gtgagctgat    7920
accgctcgcc gcagccgaac gaccgagcgc agcgagtcag tgagcgagga gcggaagag    7980 cgcccaatac gcaaaccgcc tctccccgcg cgttggccga ttcattaatg cagctggcac    8040
gacaggtttc ccgactggaa agcgggcagt gagcgcaacg caattaatgt gagttagctc    8100
actcattagg caccccaggc tttacacttt atgcttccgg ctcgtatgtt gtgtggaatt    8160
gtgagcggat aacaatttca cacaggaaac agctatgacc atgattacgc caagcgcgca    8220
attaaccctc actaaaggga acaaaagctg gagctcaata atcccgacag cagttgcatt    8280
atgatgggtt aaatgcacca gaactagcca gtcctgtgca atgcgttgca tccatgtccc    8340
gatattggac acgaacattc cacttatcca aaggcgataa ttgaagctgt tcagtgaccg    8400
gaaggttcca tggaaaagtt ttttcatcag aggctcgctc tatttttaca tgccgagcag    8460
aagcgccttg atccgctagc atcccatatt gggaggatgt ttttgtgcgc cagaaaagcg    8520
gaaaaaatat ctacgatcat agacggtcgt cagatttttcc ggtgattggc ttgttcaagc    8580
tatgcgtcaa gagcgggata tcaagcgtca tgataagaaa aaggatacag atagacgct     8640 tttgaaaaag gccatcgctg tatcctaaga gtattttagt tgataatttt tactaaataa    8700
ggcgtataac cttatgcttt tacggtaaaa tatttattat tttttattga ccgaatatgt    8760 gttttcgct ttcgcaaaga catgaatacc atttcatctc aacagaattt aactatcaat     8820
```

```
atcatgatgg aaggtatcgc aaacggctgg atcgccgcta tcaatcccgc gtttgagcca   8880
gcgcattctt tccgcagatg tgccatgagt gaaactttca ggaacggggc gcatccctgc   8940
ggctttctct aaggtatcgt cgccaatagc ctgcgctgcc cgcataccttc cttcgacatc   9000 gccctcttct atccggtcgc ggttatgcgc tgcccagact ccggcatagc aatcggcctg   9060
taattccatt ctcacctgta gggcattagc ggcagctttg ccgacattag cttgttgttc   9120
gcggatttgg tcgataagc ccattaaatc ttgcacatga tgcccgactt catgggcgat    9180
aacataggct tgggcaaaat caccgctggc aggaagcggt tgaccagttc attatagaaa   9240
tctgtatcga gataaacgcg ctgatctgct gggcagtaaa aaggcccat cgccgattct    9300 gctgcaccgc agcctgaacg acctctttga ctataaaaga ccaatgttgt cggtttatat   9360
tttttaccag catcagcgaa atcttgccc catgtgtctt cggtactagc caagacacgg    9420
caggagaaaa ggcttgcggc gttaagttgg caggcctgtt gtgccgaacg aacagaatgc   9480
acctgatgag gtgccatcgc gggttgtgtc ga                                 9512

<210> SEQ ID NO 14
<211> LENGTH: 9512
<212> TYPE: DNA
<213> ORGANISM: artificial sequence
<220> FEATURE:
<223> OTHER INFORMATION: constructed plasmid

<400> SEQUENCE: 14
ctagttcgat caacaacccg aatcctatcg taatgatgtt ttgcccgatc agcctcaatc     60
gacaatttta cgcgtttcga tcgaagcagg gatgacaatt ggctgggaac ggtatactgg    120
aataaatggt cttcgttatg gtattgatgt ttttggtgca tcggcccggg cgaatgatct    180
atatgctcat ttcggcttga ccgcagtcgg catcacgaac aaggtgttgg ccgcgatcgc    240
cggtaagtcg gcacgttaaa aaatagctat ggaatataat agctacttaa taagttagga    300
gaataaacat gcatgtacgt cctgtagaaa ccccaacccg tgaaatcaaa aaactcgacg    360
gcctgtgggc attcagtctg gatcgcgaaa actgtggaat tgatcagcgt tggtgggaaa    420
gcgcgttaca agaaagccgg gcaattgctg tgccaggcag ttttaacgat cagttcgccg    480
atgcagatat tcgtaattat gcgggcaacg tctggtatca gcgcgaagtc tttataccga    540
aaggttgggc aggccagcgt atcgtgctgc gtttcgatgc ggtcactcat tacggcaaag    600
tgtgggtcaa taatcaggaa gtgatggagc atcagggcgg ctatacgcca tttgaagccg    660
atgtcacgcc gtatgttatt gccgggaaaa gtgtacgtat caccgtttgt gtgaacaacg    720
aactgaactg gcagactatc ccgccgggaa tggtgattac cgacgaaaac ggcaagaaaa    780
agcagtctta cttccatgat ttctttaact atgccggaat ccatcgcagc gtaatgctct    840
acaccacgcc gaacacctgg gtggacgata tcaccgtggt gacgcatgtc gcgcaagact    900
gtaaccacgc gtctgttgac tggcaggtgg tggccaatgg tgatgtcagc gttgaactgc    960
gtgatgcgga tcaacaggtg gttgcaactg gacaaggcac tagcgggact ttgcaagtgg   1020
tgaatccgca cctctggcaa ccgggtgaag gttatctcta tgaactgtgc gtcacagcca   1080
aaagccagac agagtgtgat atctaccgcg ttcgcgtcgg catccggtca gtggcagtga   1140
agggcgaaca gttcctgatt aaccacaaac cgttctactt tactggcttt ggtcgtcatg   1200
aagatgcgga cttgcgtggc aaaggattcg ataacgtgct gatggtgcac gaccacgcat   1260
taatggactg gattggggcc aactcctacc gtacctcgca ttcccttac gctgaagaga   1320 tgctcgactg ggcagatgaa catggcatcg tggtgattga tgaaactgct gctgtcggct   1380
```

```
ttaacctctc tttaggcatt ggtttcgaag cgggcaacaa gccgaaagaa ctgtacagcg    1440
aagaggcagt caacgggaa actcagcaag cgcacttaca ggcgattaaa gagctgatag     1500
cgcgtgacaa aaaccaccca agcgtggtga tgtggagtat tgccaacgaa ccggataccc    1560
gtccgcaagg tgcacgggaa tatttcgcgc cactggcgga agcaacgcgt aaactcgacc    1620
cgacgcgtcc gatcacctgc gtcaatgtaa tgttctgcga cgctcacacc gataccatca    1680
gcgatctctt tgatgtgctg tgcctgaacc gttattacgg atggtatgtc caaagcggcg    1740
atttggaaac ggcagagaag gtactggaaa aagaacttct ggcctggcag gagaaactgc    1800
atcagccgat tatcatcacc gaatacgcg tggatacgtt agccgggctg cactcaatgt     1860
acaccgacat gtggagtgaa gagtatcagt gtgcatggct ggatatgtat caccgcgtct    1920
ttgatcgcgt cagcgccgtc gtcggtgaac aggtatggaa tttcgccgat tttgcgacct    1980
cgcaaggcat attgcgcgtt ggcggtaaca agaaagggat cttcactcgc gaccgcaaac    2040
cgaagtcggc ggcttttctg ctgcaaaaac gctggactgg catgaacttc ggtgaaaaac    2100
cgcagcaggg aggcaaacaa tgatctagat gactgtataa aaccacagcc aatcaaacga    2160
aaccaggcta tactcaagcc tggttttttg atggattttc agcgtggcgc aggcaggttt    2220
tatcttaacc cgacactggc gggacacccc gcaagggaca gaagtctcct tctggctggc    2280
gacggacaac gggccaagct tggaagggcc ggccaagctt gaattcgcga tcgcataact    2340
tcgtataatg tatgctatac gaagttatgc ggccgcagca caggatgacg cctaacaatt    2400
cattcaagcc gacaccgctt cgcggcgcgg cttaattcag gagttaaaca tcatgaggga    2460
agcggtgatc gccgaagtat cgactcaact atcagaggta gttggcgtca tcgagcgcca    2520
tctcgaaccg acgttgctgg ccgtacattt gtacggctcc gcagtggatg gcggcctgaa    2580
gccacacagt gatattgatt tgctggttac ggtgactgta aggcttgatg aaacaacgcg    2640
gcgagctttg atcaacgacc ttttggaaac ttcggcttcc cctggagaga gcagagattct   2700 ccgcgctgta gaagtcacca ttgttgtgca cgacgacatc attccgtggc gttatccagc    2760
taagcgcgaa ctgcaatttg gagaatggca gcgcaatgac attcttgcag gtatcttcga    2820
gccagccacg atcgacattg atctggctat cttgctgaca aaagcaagag aacatagcgt    2880
tgccttggta ggtccagcgg cggaggaact cttttgatccg gttcctgaac aggatctatt    2940
tgaggcgcta aatgaaacct taacgctatg gaactcgccg cccgactggg ctggcgatga    3000
gcgaaatgta gtgcttacgt tgtcccgcat ttggtacagc gcagtaaccg gcaaaatcgc    3060
gccgaaggat gtcgctgccg actgggcaat ggagcgcctg ccggcccagt atcagcccgt    3120
catacttgaa gctaggcagg cttatcttgg acaagaagat cgcttggcct cgcgcgcaga    3180
tcagttggaa gaatttgttc actacgtgaa aggcgagatc accaaggtag tcggcaaata    3240
atgtctaaca attcgttcaa gccgacgccg cttcgcggcg cggcttaact caagcgttag    3300
agagctgggg aagactatgc gcgatctgtt gaaggtggtt ctaagcctcg tacttgcgat    3360
ggcatcgggg caggcacttg ctgacctgcc ttaattaaat aacttcgtat aatgtatgct    3420
atacgaagtt atggccggcc aactgccacc acccataaat cccagcgggt ttattttaaa    3480
aataaaacaa atgataacca aaacgatcac gccgccgata ccgaaacggc caacgacaaa    3540
gccgagtaag ccgctaatca ggttaaaccc gccgcaccg ccgttattac caccgctaaa     3600
gtcttcacca cgttcgtctt cgacgttatc gctgcttcgg tagtcatcaa gccgcattat    3660
gcaccttccc aatttttaccc gcaggcctat ttataggccg acagcgggtt ttatctatag   3720
```

```
ctttcatttt tttgtgtttt tttgaaaaaa aacgcttgca gaacacatag ctgattgtta    3780
tacgcgcttc acacccaacg cggtgattga catagtgttc cctgatagct cagcggtaga    3840
gcgtccgact gttaatcggc aggtcgtagg ttcgaatcct actcggggag ccatttcaac    3900
gatagtcctt atagttttat tttctcttta aaaattatc ttatttccga tcaatcggtt    3960
atatttcgcc tgatagattc aagacattct gtattgggat tgtctgaata tatttcgggt    4020
agatctgttt aaagtggttt ttttgtccac tttcctaatt aggttatttc cataacgtga    4080
cccaatagcg tggccgtgag cgcttggctg ccgcggaata gggatatttt cttttttcga    4140
gataccgcca gccattaagc cattaagcca ttaagccatt aagccattaa gccattaagc    4200
cattaagcca ttaagatatc gctactcatt cttctcggcaa ggaaaaaggt gattagtcgt    4260
tatttggggt aataaatgtt tatcctcgga tcgagatttc ttgaataaag aaggacgagt    4320
ggttttcttc atttgagcct ttttctttt ttgcttttttc tatttcgctg gaaacaccccc   4380
ttttcaccta ttccagatag attgtcccct ttcgcttttt taaagcattg atcgtagaaa    4440
tcactccgat ggtcgtatga cagcgttttc tttggaaagc ggggttttac agcctttatc    4500
aatagggtca ggatggggga atcatcctct atatggagaa gtatgatgtc cctatttcg     4560
ataccctcta tccgtctgaa tgacggcaat gatttgcctg cggtaggctt tggcacctat    4620
aaactcaatg gttcggccgg tgtttccgat atcgttagcg cgattaaagt cggataccgc    4680
ttgctcgatt ctgcctttaa ttatgagaat gaaggtgctg taggcgaagc tgttcgcgag    4740
gccggtattg cccgtgataa attgcggatc gtgtccaaat taccggggcg acatcatcat    4800
tttgaagagg ccattgcaac ggtcgaggag tcacttatc gggcacagct tgattattat     4860
gatctctatc tgattcattg gcctaatccg agcaaagatc tctatgtcga ggcgtggcag    4920
gccttgattg aagcccgtaa aaagggtta atccgttcga ttggtgtctg taacttttta     4980
ccagaacatc tggaaaggct gattaaagag acgggtgtaa cgccggttgt caatcaggtg    5040
gaattgcatc cctatttcc gcaggaagag cagcgggcat gggataaagc ccatggcatt    5100
gttaccgagt catggagtcc tttgggacgt gccagcaagt tgctacagga cgacacgatt    5160
aaaaaaattg cggatcgctt gggtaagtct atcccgcaag ttattttgcg ttggcatgtc    5220
cagcttggag cgataccgat tcctaaagct tctagcaaag agcgtcagat tgaaaatcta    5280
tccttgtttg atttcgagct gtcgccgcag gatgtagaaa taatcgcgac tttagcacgg    5340
cctgatggac gcttggctga ccaagaccct gcccgctatg aagaatttta aggtacccaa    5400
ttcgccctat agtgagtcgt attacgcgcg ctcactggcc gtcgttttac aacgtcgtga    5460
ctgggaaaac cctggcgtta cccaacttaa tcgccttgca gcacatcccc ctttcgccag    5520
ctggcgtaat agcgaagagg cccgcaccga tcgcccttcc caacagttgc gcagcctgaa    5580
tggcgaatgg gacgcgccct gtagcggcgc attaagcgcg gcgggtgtgg tggttacgcg    5640
cagcgtgacc gctacacttg ccagcgccct agcgcccgct cctttcgctt tcttcccttc    5700
ctttctcgcc acgttcgccg gctttccccg tcaagctcta atcgggggc tccctttagg     5760
gttccgattt agtgctttac ggcacctcga ccccaaaaaa cttgattagg gtgatggttc    5820
acgtagtggg ccatcgccct gatagacggt ttttcgccct tgacgttgg agtccacgtt    5880
ctttaatagt ggactcttgt tccaaactgg aacaacactc aaccctatct cggtctattc    5940
ttttgattta aagggattt tgccgatttc ggcctattgg ttaaaaaatg agctgattta    6000
acaaaaattt aacgcgaatt ttaacaaaat attaacgctt acaatttagg tggcactttt    6060
cggggaaatg tgcgcggaac ccctatttgt ttatttttct aaatacattc aaatatgtat    6120
```

```
ccgctcatga gacaataacc ctgataaatg cttcaataat attgaaaaag gaagagtatg   6180
agtattcaac atttccgtgt cgcccttatt ccctttttg cggcatttg ccttcctgtt     6240 tttgctcacc cagaaacgct ggtgaaagta aaagatgctg aagatcagtt gggtgcacga   6300
gtgggttaca tcgaactgga tctcaacagc ggtaagatcc ttgagagttt tcgccccgaa   6360
gaacgttttc caatgatgag cacttttaaa gttctgctat gtggcgcggt attatcccgt   6420
attgacgccg ggcaagagca actcggtcgc cgcatacact attctcagaa tgacttggtt   6480
gagtactcac cagtcacaga aaagcatctt acggatggca tgacagtaag agaattatgc   6540
agtgctgcca taaccatgag tgataacact gcggccaact tacttctgac aacgatcgga   6600
ggaccgaagg agctaaccgc ttttttgcac aacatggggg atcatgtaac tcgccttgat   6660
cgttgggaac cggagctgaa tgaagccata ccaaacgacg agcgtgacac cacgatgcct   6720
gtagcaatgg caacaacgtt gcgcaaacta ttaactggcg aactacttac tctagcttcc   6780
cggcaacaat taatagactg gatggaggcg gataaagttg caggaccact tctgcgctcg   6840
gcccttccgg ctggctggtt tattgctgat aaatctggag ccggtgagcg tgggtctcgc   6900
ggtatcattg cagcactggg gccagatggt aagccctccc gtatcgtagt tatctacacg   6960
acggggagtc aggcaactat ggatgaacga atagacaga tcgctgagat aggtgcctca    7020
ctgattaagc attggtaact gtcagaccaa gtttactcat atatacttta gattgattta   7080
aaacttcatt tttaatttaa aaggatctag gtgaagatcc ttttgataa tctcatgacc    7140 aaaatccctt aacgtgagtt ttcgttccac tgagcgtcag accccgtaga aaagatcaaa   7200
ggatcttctt gagatccttt ttttctgcgc gtaatctgct gcttgcaaac aaaaaaacca   7260
ccgctaccag cggtggtttg tttgccggat caagagctac caactctttt tccgaaggta   7320
actggcttca gcagagcgca gataccaaat actgtccttc tagtgtagcc gtagttaggc   7380
caccacttca agaactctgt agcaccgcct acatacctcg ctctgctaat cctgttacca   7440
gtggctgctg ccagtggcga taagtcgtgt cttaccgggt tggactcaag acgatagtta   7500
ccggataagg cgcagcggtc gggctgaacg ggggggttcgt gcacacagcc cagcttggag   7560
cgaacgacct acaccgaact gagatacta cagcgtgagc tatgagaaag cgccacgctt    7620
cccgaaggga aaaggcgga caggtatccg gtaagcggca gggtcggaac aggagagcgc    7680
acgagggagc ttccaggggg aaacgcctgg tatctttata gtcctgtcgg gtttcgccac   7740
ctctgacttg agcgtcgatt tttgtgatgc tcgtcagggg ggcggagcct atggaaaaac   7800
gccagcaacg cggccttttt acggttcctg gccttttgct ggccttttgc tcacatgttc   7860
tttcctgcgt tatcccctga ttctgtggat aaccgtatta ccgcctttga gtgagctgat   7920
accgctcgcc gcagccgaac gaccgagcgc agcgagtcag tgagcgagga agcggaagag   7980
cgcccaatac gcaaaccgcc tctccccgcg cgttggccga ttcattaatg cagctggcac   8040
gacaggtttc ccgactggaa agcgggcagt gagcgcaacg caattaatgt gagttagctc   8100
actcattagg caccccaggc tttacacttt atgcttccgg ctcgtatgtt gtgtggaatt   8160
gtgagcggat aacaatttca cacaggaaac agctatgacc atgattacgc caagcgcgca   8220
attaaccctc actaaaggga acaaaagctg gagctcaata atcccgacag cagttgcatt   8280
atgatgggtt aaatgcacca gaactagcca gtcctgtgca atgcgttgca tccatgtccc   8340
gatattggac acgaacattc cacttatcca aaggcgataa ttgaagctgt tcagtgaccg   8400
gaaggttcca tggaaaagtt ttttcatcag aggctcgctc tatttttaca tgccgagcag   8460
```

```
aagcgccttg atccgctagc atcccatatt gggaggatgt ttttgtgcgc cagaaaagcg    8520
gaaaaaatat ctacgatcat agacggtcgt cagattttcc ggtgattggc ttgttcaagc    8580
tatgcgtcaa gagcgggata tcaagcgtca tgataagaaa aaggatacag gatagacgct    8640
tttgaaaaag gccatcgctg tatcctaaga gtattttagt tgataatttt tactaaataa    8700
ggcgtataac cttatgcttt tacggtaaaa tatttattat tttttattga ccgaatatgt    8760 gttttcgct ttcgcaaaga catgaatacc atttcatctc aacagaattt aactatcaat    8820
atcatgatgg aaggtatcgc aaacggctgg atcgccgcta tcaatcccgc gtttgagcca    8880
gcgcattctt tccgcagatg tgccatgagt gaaactttca ggaacggggc gcatccctgc    8940
ggctttctct aaggtatcgt cgccaatagc ctgcgctgcc cgcataccttt cttcgacatc    9000 gccctcttct atccggtcgc ggttatgcgc tgcccagact ccggcatagc aatcggcctg    9060
taattccatt ctcacctgta gggcattagc ggcagctttg ccgacattag cttgttgttc    9120
gcggatttgg tcggataagc ccattaaatc ttgcacatga tgcccgactt catgggcgat    9180
aacataggct tgggcaaaat caccgctggc aggaagcggt tgaccagttc attatagaaa    9240
tctgtatcga gataaacgcg ctgatctgct gggcagtaaa aaggcccat cgccgattct    9300 gctgcaccgc agcctgaacg acctctttga ctataaaaga ccaatgttgt cggtttatat    9360
tttttaccag catcagcgaa aatcttgccc catgtgtctt cggtactagc caagacacgg    9420
caggagaaaa ggcttgcggc gttaagttgg caggcctgtt gtgccgaacg aacagaatgc    9480
acctgatgag gtgccatcgc gggttgtgtc ga                                  9512

<210> SEQ ID NO 15
<211> LENGTH: 64
<212> TYPE: DNA
<213> ORGANISM: artificial sequence
<220> FEATURE:
<223> OTHER INFORMATION: oligo containing loxPw site and NotI site

<400> SEQUENCE: 15
ataacttcgt ataatgtatg cttattgaag catattacat acgaatacga agttatgcgg    60
ccgc                                                                 64

<210> SEQ ID NO 16
<211> LENGTH: 64
<212> TYPE: DNA
<213> ORGANISM: artificial sequence
<220> FEATURE:
<223> OTHER INFORMATION: Dna containing loxPw site and PacI site

<400> SEQUENCE: 16
ttaattaaat aacttcgtat aatgtatgct tattgaagca tattacatac gaatacgaag    60
ttat                                                                 64
```

US 9,139,818 B2

HIGH EXPRESSION ZYMOMONAS PROMOTERS

FIELD OF THE INVENTION

The invention relates to the fields of microbiology and genetic engineering. More specifically, new promoters for directing expression of chimeric genes in bacteria were identified.

BACKGROUND OF THE INVENTION

Production of ethanol by microorganisms provides an alternative energy source to fossil fuels and is therefore an important area of current research. *Zymomonas mobilis* is a natural ethanologen that can be used for commercial production of ethanol. However, *Z. mobilis* does not naturally utilize xylose, which is the major pentose in hydrolyzed lignocellulosic materials. It is desirable for an ethanologen to utilize xylose, to make full use of the carbohydrate substrates in lignocellulosic biomass hydrolysate.

*Zymomonas mobilis* and other bacterial ethanologens which do not naturally utilize xylose may be genetically engineered for xylose utilization by introduction of genes encoding 1) xylose isomerase, which catalyses the conversion of xylose to xylulose; 2) xylulokinase, which phosphorylates xylulose to form xylulose 5-phosphate; 3) transketolase; and 4) transaldolase. There has been success in engineering *Z. mobilis* strains for xylose metabolism (U.S. Pat. No. 5,514,583, U.S. Pat. No. 5,712,133, U.S. Pat. No. 6,566,107, U.S. Pat. No. 5,726,053, Feldmann et al. (1992) Appl Microbiol Biotechnol 38: 354-361, Zhang et al. (1995) Science 267:240-243), as well as a *Zymobacter palmae* strain (Yanase et al. (2007) Appl. Environ. Mirobiol. 73:2592-2599). However, typically the engineered strains do not grow and produce ethanol as well on xylose as on glucose.

For this engineering, genes encoding the heterologous proteins for xylose metabolism have been expressed from promoters that are active in *Z. mobilis* cells, typically the promoter of the *Z. mobilis* glyceraldehyde-3-phosphate dehydrogenase gene or the promoter of the *Z. mobilis* enolase gene. Strains engineered for xylose utilization have been adapted by serial passage on xylose medium, resulting in strains with improved xylose utilization as described in U.S. Pat. No. 7,223,575 and U.S. Pat. No. 7,741,119. U.S. Pat. No. 7,989,206 and U.S. Pat. No. 7,998,722 disclose *Z. mobilis* glyceraldehyde-3-phosphate dehydrogenase gene promoters with improved activities and their use for expressing xylose isomerase for xylose utilization in *Zymomonas*.

There remains a need for additional strong promoters that may be used in genetic engineering of *Zymomonas*, and other bacterial ethanologens to express genes that confer improved xylose utilization. The promoters may be used for expression of other genes as well.

SUMMARY OF THE INVENTION

The present invention provides an synthetic promoter that is a derivative of the promoter of the *Z. mobilis* glyceraldehyde-3-phosphate dehydrogenase gene, which has improved activity.

Accordingly, the invention provides an synthetic nucleic acid molecule comprising a *Z. mobilis* glyceraldehyde-3-phosphate dehydrogenase gene promoter that has a base substitution of T for C in position 90; wherein the position number is of SEQ ID NO:1. This based substitution has the effect of increasing the strength of the promoter as compared to a native *Z. mobilis* glyceraldehyde-3-phosphate dehydrogenase gene promoter.

In other aspects the invention provides a chimeric gene comprising a synthetic nucleic acid molecule having the above mentioned base substitution and a vector comprising the same.

In further aspects the invention provides a method of transforming a bacterial cell selected from the group consisting of *Zymomonas* cells and *Zymobacter* cells comprising introducing into the cell the synthetic nucleic acid molecule of the invention.

In yet another aspect the invention provides a recombinant bacterial strain selected from the group consisting of *Zymomonas* and *Zymobacter* comprising the synthetic nucleic acid molecule of the invention.

In another embodiment the invention provides a method for producing an improved synthetic glyceraldehyde-3-phosphate dehydrogenase gene promoter comprising:
 a) isolating a nucleic acid fragment comprising a glyceraldehyde-3-phosphate dehydrogenase gene promoter region from a glyceraldehyde-3-phosphate dehydrogenase gene from *Zymomonas* or *Zymobacter*;
 b) introducing in to the isolated fragment of a) a base substitution of T for C at position 90, thereby producing an improved synthetic glyceraldehyde-3-phosphate dehydrogenase gene promoter.

BRIEF DESCRIPTION OF THE FIGURES AND SEQUENCE DESCRIPTIONS

FIG. 1 shows a plasmid map of pZP13.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the native ZmPgap of the CP4 strain of *Z. mobilis*. [#1 in 4236]

SEQ ID NO:2 is the nucleotide sequence of the ZmPgap of the CP4 strain of *Z. mobilis* with a change of C to T at position 90.

SEQ ID NO:3 is the nucleotide sequence of the native ZmPgap of the ZM4 strain of *Z. mobilis*. [#2 in 4236]

SEQ ID NO:4 is the nucleotide sequence of the ZmPgap of the ZM4 strain of *Z. mobilis* with a change of C to T at position 90.

SEQ ID NO:5 is the nucleotide sequence of the ZmPgap of pZB4
 [T del #3 in 4236]

SEQ ID NO:6 is the nucleotide sequence of the ZmPgap of pZB4 with a change of C to T at position 90.

SEQ ID NO:7 is the nucleotide sequence of the ZmPgap of the ZM4 strain of *Z. mobilis* with the deletion of T at position 285 as in pZB4 and with a change of C to T at position 90.

SEQ ID NO:8 is the nucleotide sequence of the 1,951-bp DP1341-U fragment.

SEQ ID NO:9 is the nucleotide sequence of the 1,255-bp DP1341-D fragment.

SEQ ID NO:10 is the nucleotide sequence of the GUS coding sequence.

SEQ ID NO:11 is the nucleotide sequence of the E. coli araD 3'
UTR.

SEQ ID NO:12 is the nucleotide sequence of the Spec-R expression cassette.

SEQ ID NO:13 is the nucleotide sequence of pZP1332.

SEQ ID NO:14 is the nucleotide sequence of pZP1337.

SEQ ID NO:15 is the nucleotide sequence of the loxPw fragment that is 5' to the Spec-R expression cassette.

SEQ ID NO:16 is the nucleotide sequence of the loxPw fragment that is 3' to the Spec-R expression cassette.

The flanking loxPw sequences, which include the loxPw sites and restriction sites, are SEQ ID NOs:15 and 16.

DETAILED DESCRIPTION

The following definitions may be used for the interpretation of the claims and specification:

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "xylose isomerase" refers to an enzyme that catalyzes the interconversion of D-xylose and D-xylulose. Xylose isomerases (XI) belong to the group of enzymes classified as EC 5.3.1.5.

The term "xylulokinase" refers to an enzyme that phosphorylates xylulose to form xylulose 5-phosphate.

The terms "transketolase" and "transaldolase" refer to two enzymes of the pentose phosphate pathway which convert xylulose 5-phosphate to intermediates that couple pentose metabolism to the glycolytic Entner-Douderoff pathway permitting the metabolism of xylose to ethanol.

The term "gene" refers to a nucleic acid fragment that expresses a specific protein or functional RNA molecule, which may optionally include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "expression", as used herein, refers to the transcription and stable accumulation of coding (mRNA) or functional RNA derived from a gene. Expression may also refer to translation of mRNA into a polypeptide. "Overexpression" refers to the production of a gene product in transgenic organisms that exceeds levels of production in normal or non-transformed organisms.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

The term "heterologous" means not naturally found in the location of interest. For example, a heterologous gene refers to a gene that is not naturally found in the host organism, but that is introduced into the host organism by gene transfer. For example, a heterologous nucleic acid molecule that is present in a chimeric gene is a nucleic acid molecule that is not naturally found associated with the other segments of the chimeric gene, such as the nucleic acid molecules having the coding region and promoter segments not naturally being associated with each other.

As used herein, an "synthetic nucleic acid molecule" is a man made or manipulated polymer of RNA or DNA that is single- or double-stranded, optionally containing synthetic, non-natural or altered nucleotide bases. A synthetic nucleic acid molecule in the form of a polymer of DNA may be comprised of one or more segments of cDNA, genomic DNA or synthetic DNA.

The term "Z. mobilis glyceraldehyde-3-phosphate dehydrogenase gene promoter" and "ZmPgap" refer to a nucleic acid molecule with promoter activity that has a nucleotide sequence that naturally occurs upstream of the glyceraldehyde-3-phosphate dehydrogenase coding region in the Z. mobilis genome. These terms refer to the promoters of strains of Z. mobilis such as the CP4 and ZM4 strains (SEQ ID NOs:1 and 2, respectively) and to variants in sequence and/or length that direct expression at a level that is not substantially different, such as the ZmPgap of pZB4 (SEQ ID NO:3).

Standard recombinant DNA and molecular cloning techniques used here are well known in the art and are described by Sambrook, J., Fritsch, E. F. and Maniatis, T. *Molecular Cloning: A Laboratory Manual*, 2$^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

The present invention relates to synthetic, derivative promoters for expression of chimeric genes in *Zymomonas, Zymobacter*, and related bacteria. The promoters have higher expression as compared to the native promoter from which they are derived and are useful for genetic engineering for expressing coding regions or regulatory RNA in *Zymomonas, Zymobacter*, and related bacteria to obtain high levels of expressed proteins or regulatory RNAs. For example, the present promoters may be used in genetic engineering to obtain improved xylose utilization by *Zymomonas* cells by expression of a coding region for an enzyme of a xylose utilization pathway, such as xylose isomerase.

Improved Glyceraldehyde-3-Phosphate Dehydrogenase Gene Promoters

The present promoters are derivatives of the promoter from the *Z. mobilis* glyceraldehyde-3-phosphate dehydrogenase gene (ZmPgap) that have a substitution of T for C at position 90 in the ZmPgap, with position 90 referring to nucleotide +90 in SEQ ID NO:1. Promoters with this nucleotide change have increased activity as compared to the native ZmPgap.

In one embodiment the present promoter has the nucleotide sequence of SEQ IN NO:2, which is identical to SEQ ID NO:1 with the exception of a T at position 90.

In various embodiments, the present promoter is any ZmPgap having a substitution of T for C at position 90 in reference to the nucleotides of SEQ ID NO:1. The sequence of ZmPgap is not a single sequence, but may have some variation in sequence that has no substantial effect on promoter function. Having no substantial effect on promoter function means that the promoter sequence directs an expression level that is substantially similar to the level of expression directed by a ZmPgap present in a natural *Zymomonas mobilis* strain. Variation in sequence may naturally occur between different isolates or strains of *Zymomonas mobilis*, such as the difference between the ZmPgap of the CP4 and ZM4 strains at position 276 in reference to the nucleotides of SEQ ID NO:1, where in CP4 there is an A and in ZM4 there is a G (SEQ ID NOs:1 and 3, respectively. In one embodiment the present promoter has the sequence of the ZmPgap of the ZM4 strain with the substitution of T for C at position 90 (SEQ ID NO:4).

In addition, there may be one or more insertion or deletion in the ZmPgap sequence which has no substantial effect on promoter function, such as exists in the pZB4 vector. The ZmPgap of the pZB4 vector is missing the T at position 285 in reference to the nucleotides of SEQ ID NO:1, giving SEQ ID NO:5. This promoter has an A at position 276 as in the CP4 strain. In one embodiment the present promoter has the sequence of the ZmPgap of the pZB4 vector with the substitution of T for C at position 90 (SEQ ID NO:6).

With one or more insertion or deletion, position number with respect to SEQ ID NO:1 may be affected, depending on whether an insertion or deletion occurs between the 5' end of the promoter and what is position 90 in SEQ ID NO:1. Thus the position for the C to T change can best be recognized by the sequence context. The context for the C to T change is: CAGGGA<u>C</u>GACAAT where the bold and underlined C is the nucleotide changed to T in the present derivative promoter. One skilled in the art will readily recognize a change from C to T, also called a substitution of T for C, at this nucleotide, which is called position 90 with respect to SEQ ID NO:1.

In another embodiment the present promoter has the substitution of T for C at position 90, the missing T at position 285 as in pZB4, and the G at position 276 as in the ZM4 strain (SEQ ID NO:7). A promoter with the substitution of T for C at position 90, the missing T at position 285 as in pZB4, and the A at position 276 as in the CP4 strain is the same as SEQ ID NO:6. All positions are with reference to SEQ ID NO:1. Thus examples of the present promoter include SEQ ID NOs: 2, 4, 6, and 7. A ZmPgap having a substitution of T for C at position 90, including in the context given above, are called herein PgapU or $P_{gapU}$.

Preparing an Improved PgapU

The described substitution at position 90 may be introduced into a ZmPgap nucleic acid molecule by any method known to one skilled in the art. For example, an oligonucleotide having the mutation and surrounding DNA sequence may be synthesized and cloned into a larger promoter DNA fragment, substituting for a segment without the position 90 substitution. Primers containing the nucleotide change and some adjacent promoter sequence may be synthesized and used in PCR to prepare the promoter fragment. An entire promoter DNA fragment may be synthesized as multiple oligonucleotides that are ligated together. Site-directed mutagenesis may be used to introduce the nucleotide substitution.

Improved Pgap in Chimeric Genes and Vectors, Introduction into Bacterial Cells

The present promoter may be operably linked to a heterologous nucleic acid molecule that is to be expressed in a bacterial cell, forming a chimeric nucleic acid molecule, or chimeric gene which is another aspect of the present invention. The designing and construction of chimeric genes are well known to one skilled in the art. A chimeric gene typically includes a promoter, a heterologous nucleic acid molecule to be expressed, and a 3' termination control region. Termination control regions may be derived from various genes, and are often taken from genes native to a target host cell. The operably linked heterologous nucleic acid molecule may be any nucleic acid molecule whose expression is desired in a bacterial cell, including, for example, a coding region for a protein or peptide, or a nucleic acid for expression of a functional RNA. Functional RNAs include, for example, antisense RNAs, ribozymes, and interfering RNAs. In addition an operon may be constructed that comprises the promoter described herein and multiple coding regions expressed from the promoter.

The promoters described herein may be used in chimeric genes for expression in bacteria belonging to *Zymomonas* or *Zymobacter*. The chimeric genes may be used for expression of any protein involved in production of a product of *Zymomonas* or *Zymobacter*. For example, one or more enzymes involved in synthesis of an amino acid such as alanine or of sorbitol or xylitol may be expressed from a chimeric gene having these promoters. The chimeric genes may be expressed in a natural *Zymomonas* or *Zymobacter* strain that does not utilize xylose, or in a xylose-utilizing strain. Also the promoters described herein may be used for expression of enzymes related to xylose metabolism or another metabolic pathway.

The chimeric genes described herein are typically constructed in or transferred to a vector for further manipulations. Vectors are well known in the art. Certain vectors are capable of replicating in a broad range of host bacteria and can be transferred by conjugation. The complete and annotated sequence of pRK404 and three related vectors: pRK437, pRK442, and pRK442(H) are available. These derivatives have proven to be valuable tools for genetic manipulation in gram-negative bacteria (Scott et al., *Plasmid* 50(1):74-79 (2003)).

Other well-known vectors may be used in different target host cells. Particularly useful for expression in *Zymomonas* are vectors that can replicate in both *E. coli* and *Zymomonas*, such as pZB188 which is described in U.S. Pat. No. 5,514,583. Vectors may include plasmids for stable autonomous replication in a cell, and plasmids for carrying constructs to be integrated into bacterial genomes. Plasmids for DNA integration may include transposons, regions of nucleic acid sequence homologous to the target bacterial genome, or other sequences supporting integration. An additional type of vector may be a transposome produced using, for example, a system that is commercially available from EPICENTRE®. It is well known how to choose an appropriate vector for the desired target host and the desired function.

A promoter described herein may also be constructed in a vector without an operably linked nucleic acid molecule for expression, and integrated adjacent to an endogenous coding region to replace an endogenous promoter in a bacterial genome or to add a promoter, for example to a coding region within an operon. Chromosomal promoter replacements may be accomplished using methods such as described by Yuan et al (Metab. Eng. (2006) 8:79-90), and White et al. (Can. J. Microbiol. (2007) 53:56-62).

Vectors comprising a promoter described herein may be introduced into a bacterial cell by well known methods, such as using freeze-thaw transformation, calcium-mediated transformation, electroporation, or conjugation.

Expression of Heterologous Nucleic Acid Molecules Using PgapU

Increased levels of chimeric gene expression may be obtained using an improved Pgap described herein. As shown in Example 3 herein, expression of a chimeric gene containing the present promoter operably linked to a coding region gave over 4-fold increased activity of the expressed protein in a cell extract, as compared to activity of the protein expressed from the native Pgap.

In various embodiments, one or more sequences encoding a protein that improves xylose or arabinose utilization may be expressed as part of a chimeric gene including the present promoter. Coding regions that may be expressed in a xylose utilization pathway include xylose isomerase, xylulokinase, transketolase, and transaldolase. These enzymes, their encoding sequences, and their participation in a xylose utilization pathway are well-known. In particular, any xylose isomerase as disclosed in U.S. Pat. No. 7,998,722, which is incorporated herein by reference, is a xylose isomerase that may be expressed by operably linking its coding sequence to the present promoter.

In addition, for arabinose utilization, coding regions that may be expressed include L-arabinose isomerase to convert L-arabinose to L-ribulose, L-ribulokinase to convert L-ribulose to L-ribulose-5-phosphate, and L-ribulose-5-phosphate-4-epimerase to convert L-ribulose-5-phosphate to D-xylulose as disclosed in U.S. Pat. No. 5,843,760, which is herein incorporated by reference. Additionally, sequences encoding other proteins that improve xylose utilization may be expressed, such as ribose-5-phosphate isomerase (RPI) which catalyzes the interconversion of ribulose-5-phosphate and ribose-5-phosphate and belongs to the group of enzymes classified as EC 5.3.1.6 (disclosed in US 20120156746, which is incorporated herein by reference) and ribulose-phosphate 3-epimerase (RPE) which catalyzes the interconversion of D-ribulose 5-phosphate and D-xylulose 5-phosphate and belongs to the group of enzymes classified as EC 5.1.3.1 (disclosed in US 20130157331, which is incorporated herein by reference).

In one embodiment the present promoter is used to express a heterologous nucleic molecule that encodes xylose isomerase for directing increased expression of xylose isomerase, as compared to expression from the ZmPgap. The improved Pgap and xylose isomerase coding region form a chimeric gene, which also generally includes a 3' termination control region. Termination control regions may be derived from various genes, and are often taken from genes native to a target host cell. The construction of chimeric genes is well known in the art.

Any xylose isomerase coding region may be used in a chimeric gene to express xylose isomerase from an improved PgapU. Xylose isomerase enzymes belong to the group EC5.3.1.5. Examples of suitable xylose isomerase proteins and encoding sequences that may be used are disclosed in U.S. Pat. No. 7,998,722 and US 20110318801, which are incorporated herein by reference.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" or "mL" means milliliter(s), "4" means microliter(s), "µg" means microgram(s), "ng" means nanogram(s), "mg" means milligram(s), "mM" means millimolar, "µM" means micromolar, "nm" means nanometer(s), "µmol" means micromole(s), "pmol" means picomole(s), "XI" is xylose isomerase, "nt" means nucleotide.

Standard recombinant DNA and molecular cloning techniques used here are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987), Example 1

Construction of Promoter-GUS Test Integration Vectors

For integration of DNA in the *Zymomonas mobilis* genome, the pZP13 Double Cross Over (DCO) suicide vector was constructed. FIG. 1 shows its schematic map. This plasmid has a pBluescript backbone, containing an *E. coli* replication site but no *Z. mobilis* replication site. Therefore, it cannot be propagated in *Z. mobilis*. Two fragments in pZP13 that target genomic recombination, DP1341-U and DP1341-D, were synthesized from *Z. mobilis* genomic DNA by PCR. Sequences referred to are in the *Z. mobilis* genome sequence: Seo et al. (2005) Nat. Biotechnol. 23:63-68; NCBI Reference: NC_006526.2). The 1,951-bp DP1341-U fragment (SEQ ID NO:8) includes the first 217 bp (from nt-1 to nt-217) of the ZMO1250 coding sequence and 1,734-bp of upstream sequence. The 1,255-bp DP1341-D fragment (SEQ ID NO:9) includes the last 704 bp (from nt-218 to nt-921) of the ZMO1250 coding sequence and 551-bp of downstream sequence. These two fragments direct integration of transgenes located between them into the ZMO1250 coding sequence between nt-217 and nt-218 in the *Z. mobilis* genome. ZMO1250 is an open reading frame located in the *Z. mobilis* genomic sequence from 1,355,129 to 1,356,049, encoding a 306-aa hypothetical protein.

pZP13 was constructed to also include a chimeric GUS expression cassette located between the targeting fragments, which was used as a reporter to determine the strength of a test promoter. It consists of a test promoter sequence (Pro) bounded by SpeI and NsiI sites, a 1,815-bp β-glucuronidase coding sequence (GUS; SEQ ID NO:10), and a 166-bp *E. coli* araD 3'UTR (ECaraD 3'UTR; SEQ ID NO:11). Located between the targeting fragments is also a 1,014-bp Spec-R expression cassette (SEQ ID NO:12) for selection of transformed *Z. mobilis* cells using spectinomycin, flanked by loxPw fragments. The flanking loxPw sequences, which include the loxPw sites and restriction sites, are SEQ ID NOs:15 and 16.

Test promoters used to express the GUS coding region were the *Z. mobilis* glyceraldehyde-3-phosphate dehydrogenase gene ($P_{gap}$) and a derivative of this promoter, $P_{gapU}$. $P_{gap}$ is a strong 305-bp glycolytic promoter (SEQ ID NO:1), which has been used previously for expressing of xylose-utilization genes in recombinant *Z. mobilis* strains. $P_{gapU}$ is a 305-bp derivation of $P_{gap}$ (SEQ ID NO:2) that has a change from C to T at position of 90 of the promoter sequence. The pZP13 suicide vectors containing these promoters driving expression of GUS were named pZP1332 containing $P_{gap}$ (SEQ ID NO:13) and pZP1337 containing $P_{gapU}$ (SEQ ID NO:14).

Example 2

Integration of Promoter-GUS Expression Cassettes

The test promoter-GUS chimeric genes were integrated into the genome of the wild type *Z. mobilis* strain ZW1 (ATCC #31821). Competent cells were prepared by growing ZW1 overnight in MRM3G5 (1% yeast extract, 15 mM $KH_2PO_4$, 4 mM $MgSO_4$, and 50 g/L glucose) at 30° C. with 150 rpm shaking. The $OD_{600}$ value was measured using a Shimadzu UV-1200 Spectrophotometer (Kyoto, Japan). Cells were harvested and resuspended in fresh medium to an $OD_{600}$ value of 0.05. Cells were grown under the same conditions to early-middle log phase ($OD_{600}$ near 0.5), then harvested and washed twice with ice-cold water and once with ice-cold 10% glycerol. The resulting competent cells were collected and resuspended in ice-cold 10% glycerol to an $OD_{600}$ value near 100. Since transformation of *Z. mobilis* requires non-methylated DNA, pZP1332 and pZP1337 were first transformed into *E. coli* SCS110 competent cells (Stratagene, La Jolla, Calif.). For each transformation, one colony of transformed cells was grown in 10 mL LB-Amp100 (LB broth containing 100 mg/L ampicillin) overnight at 37° C. DNA was prepared from each 10 mL-culture, using QIAprep Spin DNA Miniprep Kit (Qiagen, Valencia, Calif.).

Approximately 1 µg of non-methylated plasmid DNA was mixed with 50 µL of ZW1 competent cells in a 1 MM Electroporation Cuvette (VWR, West Chester, Pa.). The plasmid DNA was electroporated into the cells at 2.0 KV using a BT720 Transporater Plus (BTX-Genetronics, San Diego, Calif.). Transformed cells were recovered in 1 mL MMG5 medium (50 g/L glucose, 10 g/L yeast extract, 5 g/L tryptone, 2.5 g/L $(NH_4)_2SO_4$, 2 g/L $K_2HPO_4$, and 1 mM $MgSO_4$) for 4 hours at 30° C. and grown on MMG5-Spec250 plate (MMG5 with 250 mg/L spectinomycin and 15 g/L agar) for 3 days at 30° C., inside an anaerobic jar with an AnaeroPack (Mitsubishi Gas Chemical, New York, N.Y.). The spectinomycin-resistant colonies were obtained and streaked onto a fresh MMG5-Spec250 plate, and grown under the same conditions as described above, indicating that the chimeric GUS/Spec-R transgene construct had been integrated into the genome of ZW1. To further confirm integration and expression of the GUS expression cassette, transformants were inoculated into 5 mL MRM3G5-Spec200 (MRM3G5 with 200 mg/L spectinomycin) in a 14 mL capped Falcon tube and grown overnight at 30° C. on a 150 rpm shaker. Cells of 100 μL cultures were spun down in a 1.5 mL microcentrifuge tube. The collected cells were washed with 1 mL 0.1 M pH 7.0 phosphate buffer and then resuspended in 100 μL GUS staining solution (1 mL solution includes 500 μL 0.2 M sodium phosphate buffer, pH 7.0, 20 μL 0.5 M EDTA, pH8.0, 10 μL 10% triton X-100, 20 μL 50 mg/mL X-Glue dimethylformamide solution, 450 μL water). Color reactions were carried out by incubating the resuspension overnight at 37° C. The reactions were stopped by removing the GUS solution and adding 100 μL of 70% EtOH. Many transformants had positive GUS staining as determined by the signature blue color. Therefore, these transformants not only had integration of chimeric GUS/Spec-R construct, but also expression of both GUS and Spec-R transgenes. These transformants were named as ZW1-ZP1332 and ZW1-ZP1337.

Example 3

Promoter Comparison by GUS Activity Assay

To measure GUS activity, two transformants containing ZW1-ZP1332 (ZW1-ZP1332 #11 and #12) or ZW1-ZP1337 (ZW1-ZP1337 #1 and #8) were grown overnight in 2 mL MRM3G5-Spec200 at 30° C. with 150 rpm shaking. Then 50 μL cultures were added into 5 mL fresh MRM3G5-Spec200 and grown 16 hrs at 30° C. with 150 rpm shaking in a 14 mL capped Falcon tube, until $OD_{600}$ was near 6. Cells were collected by centrifuge, washed with 1 mL GUS assay base buffer (50 mM $NaPO_4$ buffer, pH7.0, 1 mM EDTA) twice, resuspended in 1 mL protein extract buffer (GUS assay base buffer containing 5% glycerol). Each cell suspension was placed in a BIO101 2 mL capped tube containing Lysing Matrix A beads (BIO101, La Jolla, Calif.) and shaken 3 times on a BIO101 Fastprep FP1200 at Step 5 for 20 second. Cell debris and beads were spun down in a micro-centrifuge, and the supernatant was collected as protein extract.

Protein concentration in the extract was determined using Pierce Coomassie Protein Assay Solution (Thermo Fisher Scientific Inc., Rockford, Ill.). In the assay, 10 μL standard BSA solutions, including 0.025, 0.05, 0.1, and 0.2 μg/μL, as well as properly diluted protein extracts, were mixed with 200 μL Protein Assay Solution in a 96-well plate and incubated for 5 min at room temperature. $OD_{595}$ was measured on a Victor III (Perkin Elmer, Waltham, Mass.) and protein concentration was calculated by the instrument according to the resultant standard curve. Table 1 is a summary of protein concentrations in all extracts.

TABLE 1

Protein concentrations in cell extracts

| Promoter | ZW1-ZP Strain | Protein Concentration (ng/μL) |
|---|---|---|
| $P_{gap}$ | 1332-11 | 798 |
|  | 1332-12 | 539 |

TABLE 1-continued

Protein concentrations in cell extracts

| Promoter | ZW1-ZP Strain | Protein Concentration (ng/μL) |
|---|---|---|
| $P_{gapU}$ | 1337-1 | 705 |
|  | 1337-8 | 1,000 |

A protocol for GUS activity assay was adapted from GUS Protocols: Using the GUS as a Reporter of Gene Expression (Ed. Sean R. Gallagher, Academic Press, Inc., 1992). It was modified to perform in a 96-well plate.

In the assay, the ZW1-ZP1332 #11 and #12 protein extracts were diluted 20 times and the ZW1-ZP1337 #1 and #8 protein extracts were diluted 80 times using the protein extract buffer (GUS assay base buffer with 5% glycerol). Fresh GUS assay working buffer was prepared by mixing 3,930 μL GUS assay base buffer, 20 μL 1 M DTT, and 50 μL 100 mM p-Nitrophenyl-β-D-glucuronide (PNPG) and pre-warmed to 37° C. A Falcon 96-well flat bottom plate was also prepared by adding 200 μL 0.4 M $Na_2CO_3$ stop solution to each well. A GUS assay reaction was assembled in a 0.2 mL PCR tube by adding 25 μL diluted protein extract and 100 μL pre-warmed GUS working buffer, and then incubated at 37° C. At 15, 30, 45, and 60 min, 25 μL of reaction was removed from the reaction tube and immediately mixed with 200 μL stop solution in the prepared 96-well plate. Three parallel reactions were carried out for each protein extract. A mixture of 20 μL GUS assay working buffer and 5 μL protein extract buffer was added to a well as a blank. After completion of reaction, the 96-well plate was scanned on a Victor III plate reader to determine $OD_{405}$ in each well. Reading of the blank was deducted from each reaction. Average $OD_{405}$, which reflects the release of 4-Nitrophenol by β-glucuronidase, was plotted against reaction time, resulting in a slope S ($OD_{405}$/min) that indicates change of $OD_{405}$ per minute. Finally, reaction rate R ($OD_{405}$/ug protein/min) was calculated based on the reaction slope S and protein amount added into reaction. Reaction slope (S) and rate (R) of each protein extract are given in Table 2 below. Average reaction rates were used to calculate relative activities, which indicate promoter strength relative to $P_{gap}$. The result demonstrated that the $P_{gapU}$ promoter had strength of approximately 4.4 fold higher than the $P_{gap}$ promoter.

TABLE 2

Relative promoter strength of $P_{gapU}$ and $P_{gap}$

| Promoter | ZW1-ZP strain | S ($OD_{405}$/min) | R ($OD_{405}$/μg prot./min) | Relative activity |
|---|---|---|---|---|
| $P_{gap}$ | 1332-11 | 0.0065 | 0.033 | 100% |
|  | 1332-12 | 0.0052 | 0.039 |  |
| $P_{gapU}$ | 1337-1 | 0.0065 | 0.144 | 442% |
|  | 1337-8 | 0.0113 | 0.174 |  |

What is claimed is:

1. A synthetic nucleic acid molecule comprising a *Z. mobilis* glyceraldehyde-3-phosphate dehydrogenase gene promoter having a base substitution of T for C in position 90, where position 90 is referenced to the native *Z. mobilis* glyceraldehyde-3-phosphate dehydrogenase gene promoter of SEQ ID 1.

2. The synthetic nucleic acid molecule of claim 1 comprising a *Z. mobilis* glyceraldehyde-3-phosphate dehydrogenase gene promoter sequence selected from the group consisting of SEQ ID NOs:2, 4, 6, and 7.

3. A chimeric gene comprising the synthetic nucleic acid molecule of claim 1 or 2 operably linked to a heterologous nucleic acid molecule.

4. The chimeric gene of claim 3 wherein the heterologous nucleic acid molecule encodes a protein or peptide.

5. The chimeric gene of claim 3 wherein the heterologous nucleic acid molecule codes for a regulatory RNA molecule selected from the group consisting of an antisense RNA, a ribozyme, and an interfering RNA.

6. A vector comprising the synthetic nucleic acid molecule of claim 1 or 2.

7. A method of transforming a bacterial cell selected from the group consisting of *Zymomonas* cells and *Zymobacter* cells comprising introducing into the cell the synthetic nucleic acid molecule of claim 1 or 2.

8. A method according to claim 7 wherein introducing comprises integrating the synthetic nucleic acid molecule of claim 1 or 2 into the genome of the cell or maintaining on a stably replicating plasmid within the cell.

9. A recombinant bacterial strain comprising the synthetic nucleic acid of claim 1 or 2 wherein the bacterial strain is selected from the group consisting of *Zymomonas* and *Zymobacter*.

10. The recombinant bacterial strain of claim 9 wherein said isolated nucleic acid molecule is the promoter of a chimeric gene.

11. The recombinant bacterial strain of claim 10 wherein the chimeric gene comprises an isolated nucleic acid molecule encoding an enzyme selected from the group consisting of xylose isomerase, xylulokinase, transketolase, transaldolase, L-arabinose isomerase, L-ribulokinase, L-ribulose-5-phosphate-4-epimerase, ribose-5-phosphate isomerase, and ribulose-phosphate 3-epimerase.

12. A method for producing an improved synthetic glyceraldehyde-3-phosphate dehydrogenase gene promoter comprising:
   a) isolating a nucleic acid fragment comprising a glyceraldehyde-3-phosphate dehydrogenase gene promoter region from a glyceraldehyde-3-phosphate dehydrogenase gene from *Zymomonas* or *Zymobacter*; and
   b) introducing in to the isolated fragment of a) a base substitution of T for C at position 90, thereby producing an improved synthetic glyceraldehyde-3-phosphate dehydrogenase gene promoter.

13. An improved synthetic glyceraldehyde-3-phosphate dehydrogenase gene promoter made by the process of claim 12.

* * * * *